(12) United States Patent
Marrs et al.

(10) Patent No.: US 8,167,955 B2
(45) Date of Patent: May 1, 2012

(54) CARBON FIBER REINFORCED CARBON FOAMS FOR REPAIR AND RECONSTRUCTION OF BONE DEFECTS

(75) Inventors: Brock H. Marrs, Lexington, KY (US); Rodney Andrews, Lexington, KY (US); Larry Cunningham, Jr., Lexington, KY (US)

(73) Assignee: The University of Kentucky Research Foundation, Lexington, KY (US)

( * ) Notice: Subject to any disclaimer, the term of this patent is extended or adjusted under 35 U.S.C. 154(b) by 924 days.

(21) Appl. No.: 12/057,980

(22) Filed: Mar. 28, 2008

(65) Prior Publication Data

US 2009/0248047 A1  Oct. 1, 2009

(51) Int. Cl.
*A61F 2/02* (2006.01)
(52) U.S. Cl. .................................................. 623/23.72
(58) Field of Classification Search .... 623/23.51–23.56, 623/23.72; 602/43; 424/422–424
See application file for complete search history.

(56) References Cited

U.S. PATENT DOCUMENTS

| | | | |
|---|---|---|---|
| 4,055,862 A | 11/1977 | Farling | |
| 4,135,029 A * | 1/1979 | Pfeffer | 442/367 |
| 4,714,467 A | 12/1987 | Lechner et al. | |
| 4,963,151 A * | 10/1990 | Ducheyne et al. | 623/23.62 |
| 5,282,861 A | 2/1994 | Kaplan | |
| 5,855,616 A | 1/1999 | Fournier et al. | |
| 6,165,486 A | 12/2000 | Marra et al. | |
| 6,371,985 B1 | 4/2002 | Goldberg | |
| 6,712,850 B2 * | 3/2004 | Vyakarnam et al. | 623/15.12 |
| 6,995,013 B2 | 2/2006 | Connelly et al. | |
| 7,005,135 B2 | 2/2006 | Janas et al. | |
| 7,189,409 B2 | 3/2007 | Pirhonen et al. | |
| 7,220,951 B2 | 5/2007 | Truckai et al. | |
| 7,241,486 B2 | 7/2007 | Pirhonen | |
| 2002/0120348 A1 * | 8/2002 | Melican et al. | 623/23.72 |
| 2004/0019389 A1 * | 1/2004 | Swords | 623/23.72 |
| 2005/0261678 A1 * | 11/2005 | Truckai et al. | 606/51 |

FOREIGN PATENT DOCUMENTS

EP   0 277 678   8/1988

* cited by examiner

*Primary Examiner* — Corrine M McDermott
*Assistant Examiner* — Christina Lauer
(74) *Attorney, Agent, or Firm* — King & Schickli PLLC

(57) ABSTRACT

The present invention relates to a tissue scaffold and a method of preparing a tissue scaffold for implantation. The tissue scaffold includes a body having a graphite foam core. At least a first portion of the external surface of that graphite foam core is covered by a composite material to provide additional mechanical strength to the scaffold.

12 Claims, 3 Drawing Sheets

CARBON FIBER REINFORCED CARBON FOAMS FOR REPAIR AND RECONSTRUCTION OF BONE DEFECTS

TECHNICAL FIELD AND INDUSTRIAL APPLICABILITY OF THE INVENTION

The present invention relates generally to non-biodegradable scaffolds for use in biological applications and to a method of preparing such a scaffold for implantation.

BACKGROUND OF THE INVENTION

One of the predominant issues in medicine is the repair of bone defects created by disease, malformation, or trauma. Such bone defects are currently treated through the surgical implantation of artificial or biological grafts with the purpose of regenerating and growing new bone to fill the void. To date, the implantation of allografts and autografts are the most successful treatments; however, their use is limited by potential health risks.

To replace the use of autografts and allografts, a technology must be developed that provides the mechanical stability necessary for restoring structure and function while enabling the integration of new bone tissue. The benefits of engineered devices over current technologies (i.e. autografts and allografts) are reduced risk of disease transmission, unlimited source of materials, and elimination of donor site morbidity. Thus far, biodegradable polymer and ceramic scaffolds have garnered the most attention for repair of bone defect; however, scaffolds made from carbon are another viable option. In most cases, biodegradable scaffolds do not provide the necessary mechanical support to stabilize large defect sites and sustain bone repair over lengthy periods of time. Additionally, the less than ideal strengths of biodegradable scaffolds limit their use to small defects.

The present invention relates to the utilization of porous graphite foams externally reinforced with carbon fiber as self-supporting, integrative scaffolds for the repair and reconstruction of bone defects. The known strengths of various carbon forms coupled with the inertness of carbon make carbon fiber reinforced carbon foams excellent candidates as devices for repairing and reconstructing bone defect. Non-biodegradable carbon fiber reinforced carbon foams provide mechanical support for the duration of new bone development and defect repair. The highly porous interior structure of the foam supports and promotes the viability of osteoblasts, bone producing cells, while maintaining the pore channel structure and enabling the long term delivery of natural biomolecules and nutrients throughout the structure. Additionally, mounting the carbon foam directly to the defect site and neighboring regions of bone tissue in many application s has the potential to obviate the need for load-sharing devices currently used in bone defect repair.

SUMMARY OF THE INVENTION

In accordance with the purposes of the present invention as described herein, a tissue scaffold is provided. The tissue scaffold comprises a body having a graphite foam core with a total core volume of at least 75% and an external surface. At least a first portion of the external surface of the core is covered by a composite material that provides additional mechanical strength to the scaffold. The composite material includes reinforcing fibers having a length of at least 500 microns and a carbonized binder securing the reinforcing fibers together and to the graphite foam core. In one possible embodiment at least a second portion of the external surface of the body forms a bone interface having an open cell structure for cell and tissue reception.

Further describing the invention, the reinforcing fibers have a diameter of between about 5 and about 50 microns. Further, the reinforcing fibers may be selected from a group consisting of carbon fibers, polyethylene fibers, polyaramid fibers, polymer fibers reinforced with carbon nano-tubes, carbon fibers reinforced with carbon nano-tubes and mixtures thereof.

The binder used is a carbonizable polymer resin. Such binders include but are not limited to viscose resin, polyacetylene resins, rayon, polyacrylonitrile resins, phenolic resin, furfural resin, carbon pitch and mixtures thereof.

In one possible embodiment of the tissue scaffold, the reinforcing fibers are provided in a first layer. The reinforcing fibers in this first layer may be aligned and parallel and have longitudinal axis extending in a first direction. In another possible embodiment reinforcing fibers are also provided in a second layer. The reinforcing fibers in this second layer may be aligned and parallel and have a longitudinal axis extending in a second direction wherein the second direction and the first direction form an included angle of about 90°. In still another possible embodiment the reinforcing fibers are provided in a woven mat.

In accordance with an additional aspect of the present invention, the tissue scaffold includes a fastener to secure the scaffold to a bone. In one possible embodiment the body of the scaffold carries a mounting tab and the fastener is received and held in that mounting tab. The fastener may take the form of a standard bone screw of a type known in the art.

In accordance with still another aspect of the present invention, a method is provided of preparing a tissue scaffold for tissue implantation. The method comprises the steps of: (a) shaping a graphite foam core for receipt at an implantation site, (b) treating the graphite foam core to provide a total core volume of at least 75%; (c) covering at least a portion of the exterior surface of the graphite foam core with a composite material of reinforcing fibers and binder to provide additional mechanical strength; (d) curing said binder; and (e) carbonizing the binder.

The method may further include the cleaning of the graphite foam core following shaping. Still further, the method may include the step of cleaning and sterilizing the scaffold following carbonizing. In addition, the method may include seeding the scaffold with tissue cells prior to implantation.

The treating step of the method may be further described as including the steps of soaking the graphite foam core in a carbon dioxide and nitrogen atmosphere including between about 40 and about 60 percent nitrogen, heating the graphite foam core in a furnace to a final temperature of between about 700° and about 900° C. at a heating rate of between about 5 and about 25° C. per minute and maintaining the graphite foam core at the final temperature of between about 0.5 and about 24 hours.

Alternatively, the treating step may include the steps of soaking the graphite foam core in a nitrogen and steam atmosphere including between about 0.1 and about 10.0 percent steam, heating the graphite foam core in a furnace to a final temperature of between about 700° and about 900° C. at a heating rate of between about 5 and about 25° C. per minute and maintaining the graphite foam core at the final temperature for between about 0.5 and about 24 hours.

In yet another alternative embodiment, the treating step may be further defined as including the steps of soaking the graphite foam core in a solution of water and alkali metal hydroxide; removing the water from the solution; heating the graphite foam core in a furnace under a nitrogen atmosphere to a temperature of between about 700° and about 900° C. at a heating rate of between about 5 and about 25° C. per minute; maintaining the graphite foam core at the final temperature for between about 0.5 and about 24 hours; and neutralizing the pH of the graphite foam core.

The covering step of the method may be further defined as including the steps of coating the graphite foam core with the binder and winding the reinforcing fibers in a first direction around the graphite foam core so as to form a first layer. In addition, the covering step may further include the winding of the reinforcing fibers in a second direction around the graphite foam core so as to form a second layer.

In the following description there is shown and described several preferred embodiments of the invention, simply by way of illustration of some of the modes best suited to carry out the invention. As it will be realized, the invention is capable of other different embodiments and its several details are capable of modification in various, obvious aspects all without departing from the invention. Accordingly, the drawings and descriptions will be regarded as illustrative in nature and not as restrictive.

BRIEF DESCRIPTION OF THE DRAWINGS

The accompanying drawings incorporated herein and forming a part of the specification, illustrate several aspects of the present invention and together with the description serve to explain certain principles of the invention. In the drawings.

Reference will now be made in detail to the presently preferred embodiments of the invention, examples of which are illustrated in the accompanying drawings.

DETAILED DESCRIPTION OF THE INVENTION

Figure 1:
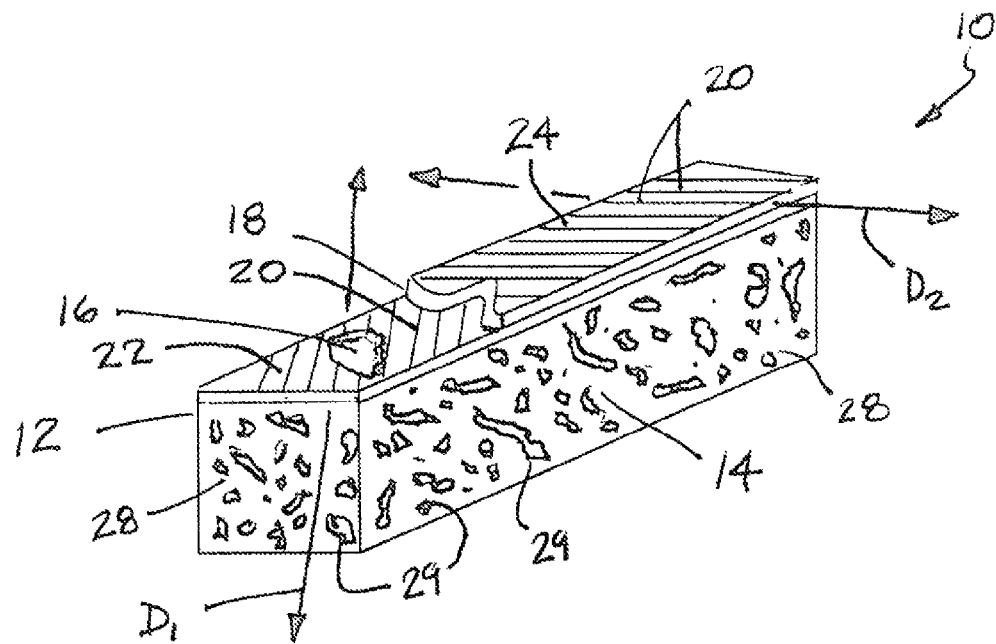
FIG. 1 is a perspective and partially fragmentary view of the tissue scaffold of the present invention.

Reference is now made to FIG. 1 illustrating one possible embodiment of the tissue scaffold 10 of the present invention. As illustrated, the tissue scaffold 10 includes a body 12 having a graphite foam core 14. The graphite foam core 14 has a total pore volume of at least 75% and an external surface. A first portion 16 of that external surface (see exposed portion of FIG. 1) is covered by a composite material 18. The composite material 18 includes reinforcing fibers 20 having a length of at least 500 microns and a carbonized binder securing the reinforcing fibers together and to the graphite foam core 144

In the FIG. 1 embodiment, the composite material 18 comprises two layers of unidirectional reinforcing fibers 20. More specifically, as illustrated the first layer 22 incorporates reinforcing fibers 20 aligned and parallel and having longitudinal axis extending in a first direction $D_1$. A second layer 24 of reinforcing fibers 20 overlies the first layer 22. The reinforcing fibers 20 in the second layer 24 are aligned and parallel and have longitudinal axis extending in a second direction $D_2$. In the illustrated embodiment the first direction $D_1$ and the second direction $D_2$ form an included angle of about 90°. It should be appreciated, however, that any included angle of the between 0 and 90° may be formed by the reinforcing fibers 20 and the two layers 22, 24. While not illustrated, it should also be appreciated that the tissue scaffold 10 may include additional layers 22, 24 incorporating directional reinforcing fibers 20 extending in substantially any desired direction.

Figure 2:
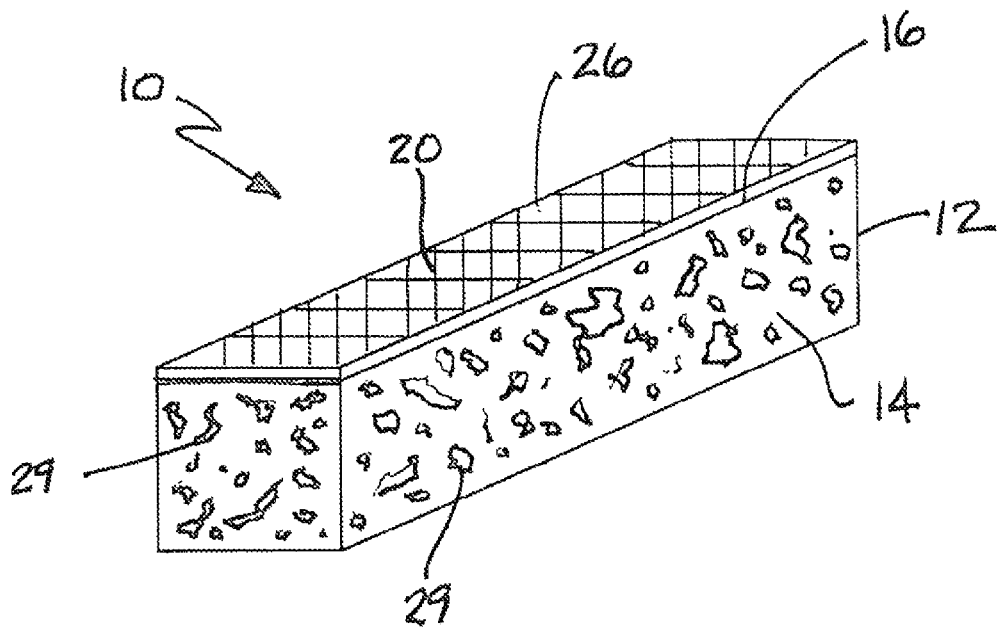
FIG. 2 is a view similar to FIG. 1 illustrating an alternative embodiment of the present invention.

In the alternative embodiment illustrated in FIG. 2, a single layer 26 of composite material overlies the first portion 16 of the external surface of the graphite foam core 14. That single layer 26 incorporates a composite material incorporating woven reinforcing fibers 20 wherein those fibers extend in two different directions.

In each of the embodiments illustrated in FIGS. 1 and 2, only the first portion 16 is covered with the composite material 18. A second external portion 28 of the graphite foam core 14 is not covered with the composite material 18. This second uncovered portion 28 of the external surface of the graphite foam core 14 forms a bone interface having an open cell structure (see cells on pores 29) for cell and tissue reception. This will be discussed in greater detail below.

Figure 4:
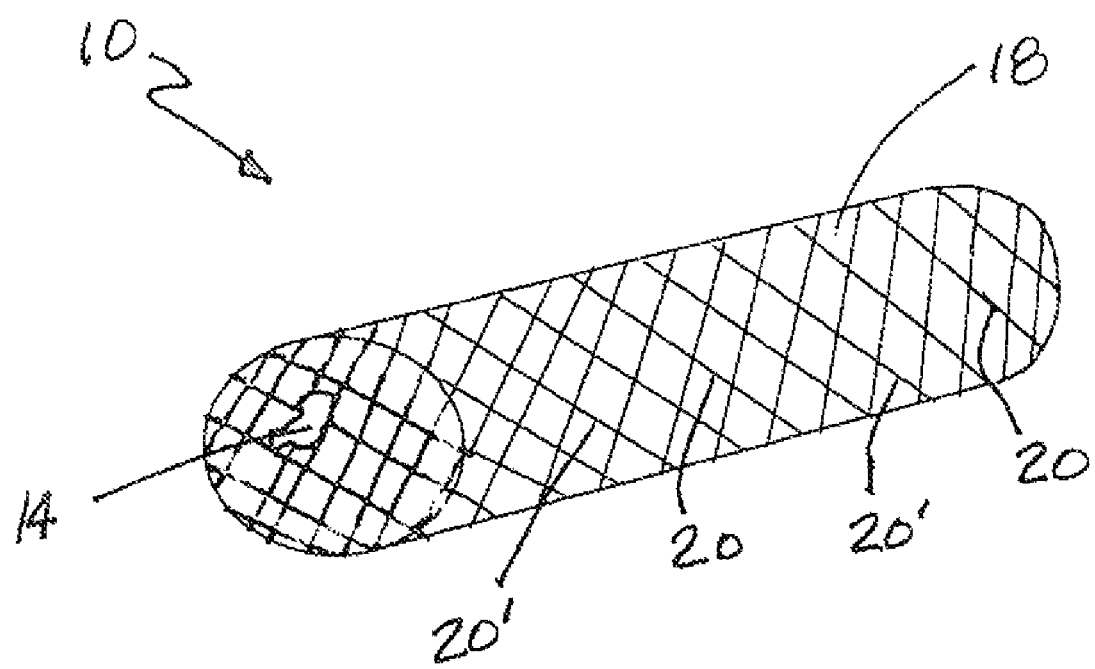
FIG. 4 is a perspective and partially fragmentary view of still another alternative embodiment of the present invention.

FIG. 4 shows yet another alternative embodiment of the tissue scaffold 10 of the present invention. In this embodiment, the scaffold 10 includes a graphite foam core 14 wherein the entire external surface is covered by a composite material 18. The illustrated composite material includes a first layer of reinforcing fibers 20 wound around the foam core 14 and extending in a first direction 131 and a second layer of reinforcing fibers 20' wound around the graphite foam core and extending in a second direction $D_2$.

Typically, the reinforcing fibers 20, 20' for the composite material 18 are made from carbon fibers, polyethylene fibers, polyaramid fibers, polymer fibers reinforced with carbon nano-tubes, carbon fibers reinforced with carbon nano-tubes and mixtures thereof. The reinforcing fibers 20 typically have a diameter of between about 5 and about 50 microns. As noted previously, the reinforcing fibers 20, 20' typically have a length of at least 500 microns. For some applications, continuous fibers may be used.

The binder of the composite material 18 is typically a carbonizable polymer resin. Such resins include, but are not limited to, polyacetylene resins, rayon, polyacrylnitrile resins, phenolic resins, viscose resins, furfural alcohol resins, polyvinyladine chloride, carbon pitches and mixtures thereof.

Figure 3A:
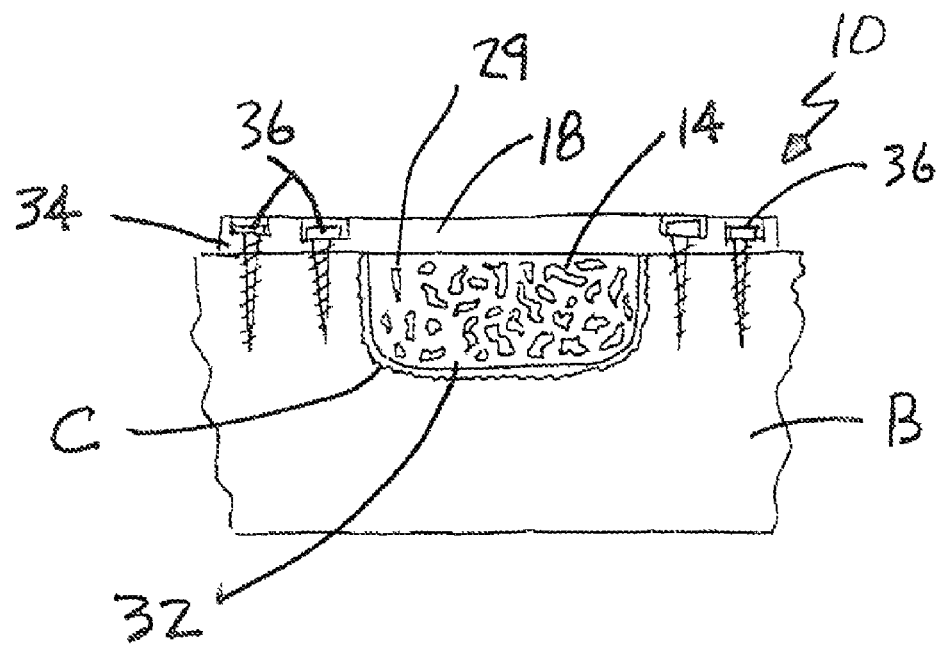
FIGS. 3A and 3B are schematical cross sectional views illustrating two ways of using the tissue scaffold of the present invention to mend a bone defect.
Figure 3B:
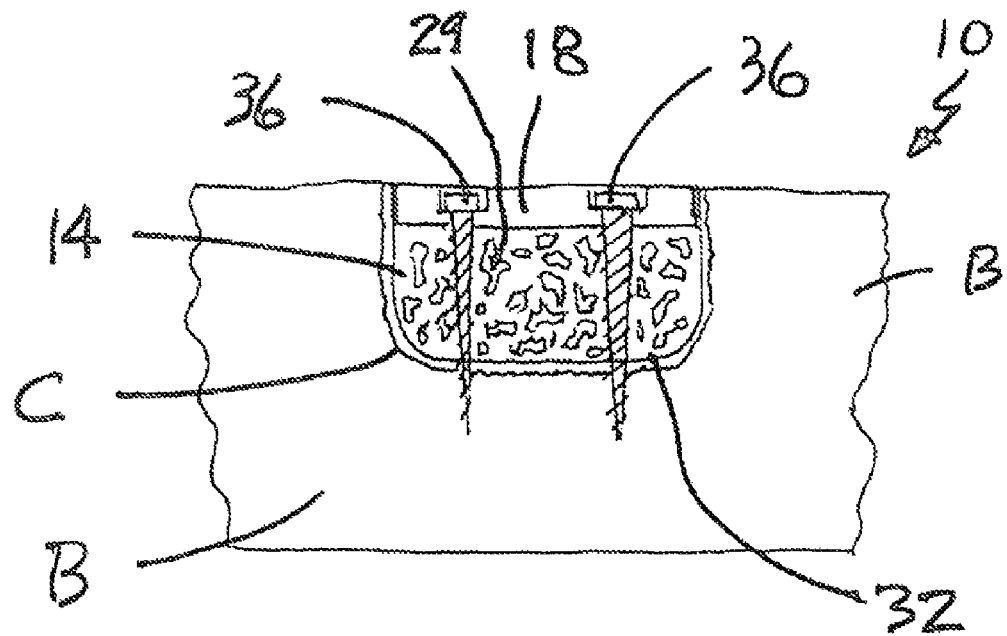

As illustrated, in FIGS. 3A and 3B, the tissue scaffold 10 may be used to mend a defect in a bone B. The tissue scaffold 10 is prepared for implantation by first shaping the graphite foam core 14 for receipt in a cavity C in the bone B at the implantation site. The graphite foam core 14 is then treated to provide a total pore volume of at least 75%. Next, the exterior surface of the foam core 14 is covered with a composite material to provide additional mechanical strength. In the illustrated embodiment, only a first portion 30 of the foam core 14 is covered with the composite material 18. The remaining portion 32 of the graphite foam core 14 is left uncovered and the cells or pores 29 are exposed. After implantation, this portion 32 forms an interface with the bone B that has an open cell structure for cell and tissue reception. After covering the first portion 30 of the exterior surface of the core 14 with composite material 18, the binder is cured and then carbonized.

As further illustrated in FIG. 3A, the tissue scaffold 10 incorporates a mounting tab 34 at each end. In the illustrated embodiment, the mounting tab 34 is formed by the composite material 18. It should be appreciated that the mounting tab could also incorporate graphite foam core 14. In yet another alternative embodiment, the mounting tab 34 may be formed by other materials such as metal. As illustrated, a series of four bone screws 36 are received in the mounting tab 34. The four bone screws 36 engage the bone B to hold the scaffold 10 in position.

In an alternative embodiment illustrated in FIG. 3B, two bone screws 36 are provided extending through the composite material 18 and the graphite foam core 14. The screws 36 engage in the bone B to secure the scaffold 10 in position.

The method of preparing the tissue scaffold 10 for implantation may be further described as including the steps of cleaning the graphite foam core 14 following shaping and cleaning and sterilizing the scaffold following carbonizing. Using current imaging techniques, a 3-dimensional digital representation of the bone defect site or site of reconstruction can be rendered. The resulting image is used to determine the actual size and shape of the defect or missing bone. A digital blueprint is then created to serve as a guide for machining. Of course, prior to implantation, bone at the defect or fracture site may be removed to ensure a close fit between the tissue scaffold 10 and the host bone B. As noted and described at FIG. 3, tabs 34 may be added to the graphite foam core 14 to overlap the neighboring host bone B in cases of reconstruction or in large defects at sites. The surgical screws 36 through the tabs 34 stabilize the tissue scaffold 10 at the site of implantation and restore structure and function quickly. In addition the method may include seeding the tissue scaffold 10 with tissue cells, such as but not limited to osteoblasts, prior to implantation.

A number of procedures may be utilized to treat the graphite foam core 14 in order to provide a total pore volume of at least 75%. In one approach, the graphite foam core 14 is soaked in a carbon dioxide and nitrogen atmosphere including between about 40 and about 60 percent nitrogen. The graphite foam core 14 is then heated in a furnace to a final temperature of between about 700° and about 900° C. at a heating rate of between about 5 and about 25° C. per minute. The graphite foam core 14 is maintained at the final temperature for between about 0.5 and about 24 hours in order to complete the treatment.

In yet another approach, the treating step includes soaking the graphite foam core 14 in a nitrogen and steam atmosphere including between about 0.1 and about 10% steam. This is followed by the heating of the graphite foam core 14 in a furnace to a final temperature of between about 700° and about 900° C. at a heating rate of between about 5 and about 25° C. per minute. Next is the maintaining of the graphite foam core at the final temperature for between about 0.5 and about 24 hours in order to complete the treatment.

In still another approach, the graphite foam core 14 is soaked in a solution of water and alkali metal hydroxide such as potassium hydroxide and/or sodium hydroxide. This is followed by removing the water from the solution. Next is the heating of the graphite foam core 14 in the furnace under a nitrogen atmosphere to a temperature of between about 700° and about 900° C. at a heating rate of between about 5 and about 25° C. per minute. This is followed by the maintaining of the graphite foam core 14 at the final temperature for between about 0.5 and about 24 hours. The pH of the graphite foam core is then neutralized in order to complete the processing.

The step of covering the external surface of the graphite foam core 14 with the composite material 18 may include the steps of coating the graphite foam core with an appropriate binder and then the positioning of a pre-cut reinforcing fiber fabric in the binder on the surface of the graphite foam core. Alternatively, the method may include the winding of reinforcing fibers 20 in a first direction around the graphite foam core so as to form a first layer 22. Of course the covering may further include the winding of reinforcing fibers 20 in a second direction around the graphite foam core 14 so as to form a second layer 24. In addition, further layers may be provided by winding or by the application of cut fabric as desired for any particular application.

The tissue scaffold 10 of the present invention forms the basic structure of an engineered tissue. The tissue scaffold 10 is biocompatible, strong, shapeable, porous, permeable and encourages cell attachment proliferation and function. The tissue scaffold 10 is permanent and will not degrade in the implant site over time. Unlike a biodegradable scaffold the tissue scaffold 10 of the present invention does not lose mechanical integrity and, accordingly, the healing process is not hindered. As such, the tissue scaffold 10 of the present invention is particularly suited for large bone defects or in instances of reconstructive surgery. The core structure of the graphite foam core 14 of the tissue scaffold 10 incorporates nanostructure passages that induce conformational changes and absorb proteins to expose cell-binding regions of amino acids such as the RGD complex that help promote the growth of new bone. More specifically, the hierarchy of pore size ranges in the graphite foam core 14 promotes the attachment, proliferation, and function of osteoblasts and encourages the development of a vascular bed while also enabling the free flow of nutrients and biomolecules throughout the foam. Since the graphite foam core 14 is non-degradable, there is little risk of the pore walls collapsing and cutting off the supply of nutrients as is the issue with some biodegradable scaffolds. Additionally, the non-degrading structure provides stability and structure for the duration of new bone grouch and integration.

Carbon fibers are particularly useful as reinforcing fibers 20 in: the tissue scaffold 10 of the present invention. The carbon fibers 20 function as a mechanism of external reinforcement for the graphite foam core 14. Carbon fibers 20 aligned directly along the direction of stress will absorb some of the strain energy associated with loading of the bone B during the knitting process. The carbon fibers 20 provide added strength and shield the inner foam core 14 from damaging stresses.

The foregoing description of the preferred embodiments of the present invention have been presented for purposes of illustration and description. It is not intended to be exhaustive or to limit the invention to the precise form disclosed. Obvious modifications or variations are possible in light of the above teachings. The embodiments were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled. The drawings and preferred embodiments do not and are not intended to limit the ordinary meaning of the claims in their fair and broad interpretation in any way.

What is claimed:

1. A tissue scaffold, comprising:
    a body having a graphite foam core with a total pore volume of at least 75% and an external surface;
    at least a first portion of said external surface being covered by a composite material that provides additional mechanical strength to said scaffold, said composite material including reinforcing fibers having a length of at least 500 microns and a carbonized binder securing said reinforcing fibers together and to said graphite foam core.

2. The tissue scaffold of claim 1, wherein at least a second portion of said external surface forms a bone interface having an open cell structure for cell and tissue reception.

3. The tissue scaffold of claim 1, wherein said reinforcing fibers have a diameter of between about 5 and about 50 microns.

4. The tissue scaffold of claim 3, wherein said reinforcing fibers are selected from a group consisting of carbon fibers, polyethylene fibers, polyaramid fibers, polymer fibers reinforced with carbon nanotubes, carbon fibers reinforced with carbon nanotubes and mixtures thereof.

5. The tissue scaffold of claim 4, wherein said binder is a carbonizable polymer resin.

6. The tissue scaffold of claim 5 wherein said carbonizable polymer resin is selected from a group of binders consisting of viscose resin, polyacetylene resin, rayon, polyacrylonitrile resin, phenolic resin, furfural alcohol resin, carbon pitch and mixtures thereof.

7. The tissue scaffold of claim 4, wherein said reinforcing fibers are provided in a first layer wherein said reinforcing fibers in said first layer are aligned in parallel and have longitudinal axes extending in a first direction.

8. The tissue scaffold of claim 7, wherein said reinforcing fibers are provided in a second layer wherein said reinforcing fibers in said second layer are aligned in parallel and have longitudinal axes extending in a second direction wherein said second direction and said first direction form an included angle of about 90°.

9. The tissue scaffold of claim 4, wherein said reinforcing fibers are provided in a woven mat.

10. The tissue scaffold of claim 1, further including a fastener for securing said scaffold to a bone.

11. The tissue scaffold of claim 10, wherein said fastener is a bone screw.

12. The tissue scaffold of claim 1, wherein said body carries a mounting tab and a fastener is received and held in said mounting tab.

* * * * *